United States Patent
Siol

(10) Patent No.: US 6,881,858 B2
(45) Date of Patent: Apr. 19, 2005

(54) ASYMMETRIC (METH)ACRYLATE CROSSLINKING AGENTS

(75) Inventor: Werner Siol, Darmstadt (DE)

(73) Assignee: ROEHM GmbH & Co. KG, Darmstadt (DE)

( * ) Notice: Subject to any disclaimer, the term of this patent is extended or adjusted under 35 U.S.C. 154(b) by 155 days.

(21) Appl. No.: 10/042,232

(22) Filed: Jan. 11, 2002

(65) Prior Publication Data

US 2002/0095016 A1 Jul. 18, 2002

(30) Foreign Application Priority Data

Jan. 13, 2001 (DE) .......................................... 101 01 389

(51) Int. Cl.⁷ .............................................. C07C 69/52
(52) U.S. Cl. ........................ 560/205; 560/204; 560/217; 560/224
(58) Field of Search ................................ 560/204, 205, 560/209, 217, 224

(56) References Cited

U.S. PATENT DOCUMENTS

| | | | | |
|---|---|---|---|---|
| 4,618,703 A | * | 10/1986 | Thanawalla et al. | 560/209 |
| 4,859,792 A | * | 8/1989 | Powanda et al. | 560/204 |
| 5,149,642 A | * | 9/1992 | Mazur et al. | 435/135 |
| 5,219,479 A | * | 6/1993 | Mathiesen et al. | 508/494 |
| 5,243,069 A | * | 9/1993 | Emmons | 560/224 |

FOREIGN PATENT DOCUMENTS

| | | |
|---|---|---|
| DE | 33 29 765 C2 | 2/1985 |
| DE | 35 10 035 A1 | 9/1986 |
| EP | 0 899 286 | 3/1999 |
| JP | 58-28718 | 2/1983 |
| JP | 58-29744 | 2/1983 |
| JP | 01087608 A | 3/1989 |
| SU | 630249 | 10/1978 |

OTHER PUBLICATIONS

John McMurry "Organic Chemistry", Brooks/Cole Publishing Company, 1988, pp. 752, 753, 758, 759.*

Patent Abstracts of Japan; vol. 012, No. 293, Jul. 6, 1989; & JP 01 087608, Mar. 31, 1989.

Patent Abstracts of Japan; vol. 007, No. 108, May 11, 1983; & JP 58 029744, Feb. 22, 1983.

Database WPI Section Ch, Week 197932, Derwent Publications Ltd., London, GB; AN 1979–59492B XP002258093 & SU 630 249 A (AS USSR HIGH MOLECU), Sep. 13, 1978.

Yasukazu Saimi et al; "Preparation and Visible Light Polymerization of Triethyleneglycol Acrylate Methacrylate"; Polymer Journal, vol. 24, No. 4, pp. 357–363; 1992.

\* cited by examiner

*Primary Examiner*—Tatyana Zalukaeva
(74) *Attorney, Agent, or Firm*—Oblon, Spivak, McClelland, Maier & Neustadt, P.C.

(57) ABSTRACT

Asymmetric (meth)acrylate crosslinking agents may be prepared by reacting a hydroxyacrylate with methacrylic anhydride to give a crosslinking agent with acrylic and methacrylic groups. Asymmetric (meth)acrylate crosslinking agents can be employed in the production of superabsorbers and thickening agents.

15 Claims, No Drawings

ASYMMETRIC (METH)ACRYLATE CROSSLINKING AGENTS

FIELD OF THE INVENTION

This invention relates to a method for preparing asymmetric (meth)acrylate crosslinking agents with the general formula (I) with x=1, 2, 3, R=H, CH$_3$, n=1–100

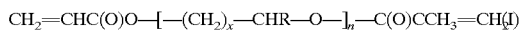

and the use of the crosslinking agents prepared by this method for the synthesis of superabsorbers and thickening agents.

DISCUSSION OF THE RELATED ART (Meth)acrylate esters of polyfunctional alcohols, for example ethylene glycol dimethacrylate, have found wide industrial use (for example, see Kirk-Othmer, Encyclopedia of Chemical Technology, Vol. 13, 331 ff). Various acrylate and methacrylate esters are generally synthesized by the esterification of the corresponding alkanols with acrylic acid or methacrylic acid or by the transesterification of methyl methacrylate or acrylates, for example.

In addition, acryloyl chloride and methacryloyl chloride are also used for the synthesis of (meth)acrylate esters. In the case of acrylate esters in particular, however, care must be taken for effective binding of liberated HCl, to prevent the formation of byproducts containing chlorine.

The synthesis of (meth)acrylate esters using anhydrides is also described. Thus, U.S. Pat. No. 5,491,244 describes the synthesis of an acrylate ester containing epoxy groups. The synthesis is accomplished without catalyst, from the corresponding epoxy alcohol and about a four-fold excess of acrylic anhydride. The synthesis of methacrylate esters starting from methacrylic anhydride and various alkanols with an additional ester function (lactate esters) is distinctly less successful. Despite catalysis with sulfuric acid, an excess of methacrylic anhydride and 5 hours of heating at 130° C., conversion of only about 50% is achieved. In addition, the separation of unreacted methacrylic anhydride presents problems (C. E. Rehberg et al., Journal of the American Chemical Society, Vol. 67, 210 (1945)). An elegant method for the synthesis of α,ω-di(meth)acryloyl-substituted polytetrahydrofuran is reported by Heitz and coworkers (U.S. Pat. No. 4,412,063). They polymerize tetrahydrofuran in the presence of acrylic or methacrylic anhydride to form polytetrahydrofuran with acrylate or methacrylate end groups.

Besides compounds with identical end groups, such as the diacrylates and dimethacrylates mentioned above, for example, divinyl compounds with double bonds of differing reactivity have also been of interest in particular. Vinyl or allyl methacrylates may be mentioned here. These so-called graft crosslinking agents, for example, are suitable for constructing multiphase plastics linked to one another, since only the methacryloyl group is copolymerized at first during the polymerization, while the allyl group takes part in the polymerization only at a later time. This makes it possible, for example, to graft polybutyl acrylate onto a polymethyl methacrylate that contains allyl groups (for example see DE-PS 3329765.7).

Crosslinking agents that have one acryloyl group and one methacryloyl group in a molecule are of particular interest. Methacryloyl and acryloyl groups differ distinctly in their copolymerization properties. For example, for the system methyl acrylate=Monomer 1, methyl methacrylate= Monomer 2, the copolymerization parameters are $r_1$=0.40, $r_2$=2.15 (for example, see Ullmann's Encyclopedia of Industrial Chemistry, Fifth Edition, Vol. A21,162), so that the methacryloyl group of the crosslinking agent molecule especially is incorporated in the chain in the initial phase of polymerization. The copolymerization behavior of the acryloyl group, however, is not so unfavorable, so that this group also is almost completely incorporated in the polymer chains during the polymerization.

Crosslinking agents with one acryloyl and one methacryloyl group in a molecule can therefore be used advantageously to make very homogeneous networks.

Thus methacryloyloxyethyl acrylate is used as a formula component for preparing soft contact lenses (JP 58 28,718). The water uptake of the contact lenses made in this way is 70.9%, compared with only 29.0% for conventional lenses.

Compounds of the type $CH_2$=$CHCO_2Z^1Z^2Z^3O_2CC(Me)$ =$CH_2(Z^1, Z^3$=$(CHCHO)_n$, (n=0–10); $Z^2$=alkyl, aryl, cycloalkyl) can be used for curable dental cements. Thus a product prepared with methacryloyloxyethyl acrylate shows compressive strength of 43.600 kg/cm$^2$ and a Brinell hardness of 40.7, compared with 33.300 kg/cm$^2$ and 27.2 when using ethylene glycol dimethacrylate (JP 0187,608).

U.S.S.R. 630,249 recommends asymmetric (meth) acrylate crosslinking agents with the formula $CH_2$=$CMeCO_2ZO_2CCH$=$CH_2[Z$=$CH_2CH_2$, $CHMeCH_2$, $CH_2CH_2OCH_2CH_2]$ to construct polymers with thermal dimensional stability. These (meth)acrylate crosslinking agents are synthesized by reacting $CH_2$=$CMeCO_2ZOH$ with $CH_2$=$CHCOCl$ in dimethylacetamide.

JP 58 29,744 describes the synthesis of methacryloyloxyethyl acrylate with a purity of 99.7% by reacting hydroxyethylacrylate with methacryloyl chloride. This is carried out below 10° C. and the HCl formed is bound by triethylamine. The (meth)acrylate monomer is used to prepare soft contact lenses.

Although asymmetrically substituted (meth)acrylate crosslinking agents are therefore of interest for constructing various polymer networks, there is as yet no suitable method for making this class of monomer. The [3-acryloxy]-2-hydroxypropyl methacrylate available on the market and which is made by reacting glycidyl methacrylate with acrylic acid, does represent an asymmetric methacrylate crosslinking agent, but this crosslinking agent is of only limited use because of its hydroxyl group and the sensitive glycerol structure. Currently there is no method for preparing suitable asymmetric crosslinking agents, especially those that provide products with no impurities containing chlorine.

SUMMARY OF THE INVENTION

It is an object of the present invention to provide a method for preparing asymmetric crosslinking agents.

It is a further object of the invention to provide a method for synthesizing superabsorbers and thickening agents that incorporate the asymmetric crosslinking agents.

The simple preparation of a mixture of asymmetric (meth) acrylate crosslinking agents (I) and methacrylic acid is another object of this invention.

DETAILED DESCRIPTION OF THE INVENTION

It has now been found that asymmetric (meth)acrylate crosslinking agents of Formula (I) with x=1,2,3, R=H, CH$_3$, n=1–100

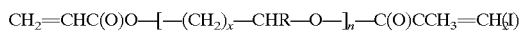

are readily available by reacting hydroxyacrylates of Formula (II)

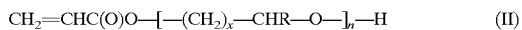

with methacrylic anhydride to form (I) and methacrylic acid.

The reaction is carried out in the presence of 0.1 to 20 wt. % of an acidic catalyst in a temperature range of 0° C. to the boiling point of the reaction mixture for a period of 0.5 to 36 hours. It is preferred that the acidic catalyst is present from 0.1 to 5 wt. %. The preferred temperature is from 0–100° C. The preferred reaction time is from 0.5–24 h. Under these conditions the esterification of (II) occurs to give (I), but the acrylate ester group is not cleaved, so that the product (I) contains only a small amount of diacrylate and dimethacrylate. The content of diacrylate and dimethacrylate is ordinarily <5 wt. %, preferably <2 wt. %. To a great extent the content of diacrylate results from diacrylate already present in the starting material (II), while the content of dimethacrylate in the end product can be attributed principally to impurities of type (III) in the starting material (II).

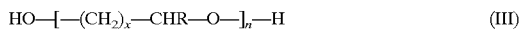

As a rule, both the diacrylate content and the dimethacrylate content in the product are <1 wt. %.

In principle, the method pursuant to the invention provides asymmetric (meth)acrylate crosslinking agents (I) free of byproducts containing chlorine. In general the content of impurities containing chlorine is <0.1 wt. %. However, care must be taken that chlorine is absent from the raw materials for this purpose. For this reason a methacrylic anhydride prepared by the method described in U.S. Pat. No. 5,491,244 from benzoyl chloride is unsuitable. More suitable as the starting material is a methacrylic anhydride that has been prepared from methacrylic acid and acetic anhydride. Such a product is described in DE-OS 3510035, for example (the portions therein relevant to the preparation of methacrylic anhydride are incorporated herein by reference). Methacrylic anhydride prepared from methacrylic acid by reaction with acetic anhydride ordinarily contains small amounts of unreacted acetic anhydride as well as the mixed anhydride of methacrylic acid and acetic acid. In general, a purity of 93%, or better 96%, is adequate for a methacrylic anhydride prepared chlorine-free. Because of the content of mixed anhydride and acetic anhydride in the methacrylic anhydride, in the reaction with the hydroxyacrylate (II), the corresponding acetate ester (IV) is obtained as an impurity.

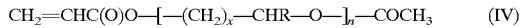

However, it has been found that in contrast to byproducts containing chlorine, contamination with <5 wt. % (IV), preferably <2 wt. % (IV), and with particular preference <1 wt. % (IV), is tolerable. Therefore, the preparation of asymmetric (meth)acrylate crosslinking agents (I) with a content of 0.2–5 wt. % (IV) is a preferred method. This makes it possible to use industrially readily available methacrylic anhydride as the starting material.

The hydroxyacrylates (II) are available on the market. Hydroxyethyl acrylate and hydroxypropyl acrylate, for example, are described by Gruber et al. (U.S. Pat. No. 3,987,090) 4-hydroxybutyl acrylate is available according to EPA 0465853 (the portions of each relevant to the production of hydroxy acrylate is incorporated herein by reference). The hydroxyacrylate may be based on a polytetrahydrofuran chain.

Regarding polyoxyalkylenes, for example, see Ullmann's Encyclopedia of Industrial Chemistry, Vol. A21, 579 (the portion thereof describing polyoxyalkylenes is incorporated herein by reference). Asymmetric (meth)acrylate crosslinking agents (I) based on a polyoxyethylene group are of particular interest. This corresponds to x=1, R=H in Formula (I). These compounds are available pursuant to the invention method by the reaction of polyethylene glycol acrylate (=polyethylene oxide acrylate; x=1, R=H in Formula (II)) with methacrylic anhydride.

Compounds with n=1–100 may be mentioned as starting materials. Of particular interest are diethylene glycol acrylate (n=2), triethylene glycol acrylate (n=3), tetraethylene glycol acrylate (n=4), and mixtures with n=2–40, especially n=4–20, and with particular preference with an average value of n in the range of 5–10. An example that may be mentioned here is polyethylene glycol acrylate with an average molecular weight $M_n$ of about 375.

Of just as much interest are asymmetric (meth)acrylate crosslinking agents (I) based on a polypropylene oxide chain. This corresponds to x=1 and R=CH$_3$ in Formula (I). The corresponding acrylate esters according to Formula (II) in the range of n=1–100 serve as starting materials. Hydroxypropyl acrylate (n=1) and the corresponding oligomers n=2–40 are of particular interest. Of special interest here also are mixtures with n=4–20 or an average n in the range of 5–10. A polypropylene glycol acrylate with an average molecular weight $M_n$ of about 475 may be mentioned by way of example Also of interest are (meth)acrylate crosslinking agents that contain both oxyethyl and oxypropyl units.

Also to be mentioned are asymmetric (meth)acrylate crosslinking agents (I) based on a polytetrahydrofuran chain (x=3, R=H in Formula (I)). Of particular interest here are 4-hydroxybutyl acrylate (n=1) and mixtures with n=2–50.

These materials are produced in a similar fashion to that employed for other compounds of Formula (I) described earlier. Acidic catalysts that are preferably used are sulfuric acid, aromatic or aliphatic sulfonic acids, which may be bound to a polymeric resin, for example, or phosphonic acids. These catalytic acids are suitably used in proportions of 0.3–5 wt. % based on the methacrylic anhydride used. A smaller proportion of catalytic acid is unsuitable, since this leads to long reaction times and side reactions.

The reaction is generally carried out for 2 to 12 h, preferably from 2 to 6 hours. The reaction temperature is generally in the range of 30–80° C., preferably from 30 to 60° C.

Adequate stabilization of the batch against polymerization is important for the success of the reaction of the hydroxyacrylates (II) to give the products (I). Sterically hindered phenols such as Topanol A or ionol may be mentioned here in particular. If the hydroxyacrylates (II) contain other stabilizers, for example hydroquinone monomethyl ether, then they are generally converted to the corresponding phenyl methacrylates. Therefore, hydroquinone monomethyl ether is unsuitable as the sole stabilizer. It is recommended to use hydroxyacrylates (II) already stabilized with sterically hindered phenols for the preparation of asymmetric (meth)acrylate crosslinking agents pursuant to the invention.

The molar ratio of methacrylic anhydride to hydroxyacrylate (II) is chosen to be about 1:1. Particularly with longer-chained molecules (n=2–10), it is advantageous to use a deficiency of methacrylic anhydride (e.g. 0.95 parts of methacrylic anhydride/1.0 part of hydroxyacrylate). This ensures complete conversion of the methacrylic anhydride so that separation of unreacted anhydride is unnecessary.

It is just as possible to use an excess of methacrylic anhydride, for example 20 mol %. In this case, after the reaction of the hydroxyacrylate (II) is as complete as possible, the excess methacrylic anhydride is destroyed by adding a low molecular weight alcohol such as methanol, ethanol, or isopropanol. This method is particularly recommended with longer-chained compounds (n=3–100). The excess methacrylic anhydride guarantees the most complete possible conversion of the hydroxy compound; the subsequent reaction of the methacrylic anhydride to give ethyl methacrylate and methacrylic acid, for example, ensures easier separation of these components with lower boiling points than methacrylic anhydride.

In principle, the methacrylic acid formed in the reaction of the hydroxy ester with methacrylic anhydride can be distilled out of the reaction batch directly. In addition, it is also possible to first carry out the reaction completely, to separate the catalyst, and only then to distill the methacrylic acid out of the batch. In any case, the methacrylic acid is separated at reduced pressure, for example with p<10 mbar. Air is fed through the reaction batch for better stabilization.

In general the methacrylic acid content is removed from the batch to a content of <5 wt. %, preferably <2 wt. %.

For the short-chained asymmetric (meth)acrylate crosslinking agents (n=1), purification of the products (I) is possible by subsequent distillation at reduced pressure, but it is preferred to prepare the compounds (I) without purification by distillation.

To do this, for example, the catalyst is separated by filtration or centrifugation; in the case of catalysts not bound to polymer, for example sulfuric acid or methanesulfonic acid, the catalyst can also be removed by washing with water. The methacrylic acid is separated by distillation, as stated above.

The product obtained in this way is generally so pure, with (meth)acrylate crosslinking agent (I) content >90, preferably >95, and with special preference >98%, that the product can be used for most applications without further purification.

Of particular interest here is the use of the (meth)acrylate crosslinking agents (I) to make two-phase polymer systems, for example PMMA-polybutyl acrylate copolymers, such as those of interest as high-impact strength modified PMMA.

Of particular importance, however, are (meth)acrylate crosslinking agents (I) that contain a residual amount of 1–40 wt. %, preferably 3–20 wt. %, of hydroxyacrylates (II). Such crosslinking agents can be prepared especially simply by using an appropriate deficiency of methacrylic anhydride. These asymmetric crosslinking agents are suitable for preparing very homogeneous, very soft, hydrophilic networks. The preparation of superabsorbers is especially amenable to the use of these cross linking agents.

Of special interest also is the use of the crosslinking agents (I) prepared by the method pursuant to the invention to prepare thickening agents dependent on pH, for example for the synthesis of emulsion polymers based on ethyl acrylate/methacrylic acid/crosslinking agent, such as those used in water-based paint formulas. In this case separation of the methacrylic acid is unnecessary. The hydroxyacrylate (II) and methacrylic anhydride are reacted in this case in a simple one-pot reaction using a catalyst, to give a mixture of asymmetric (meth)acrylate crosslinking agent and methacrylic acid.

The mixture obtained can be used directly or after separation or neutralization of the catalytic acid to prepare networks containing (meth)acrylic acid.

Thus, the formulas for such thickening agents effective in alkaline medium generally contain 10–50 wt. % methacrylic acid and 0.01–5 wt. % crosslinking agent. This alone shows that it is unnecessary to separate the methacrylic acid for such applications.

German application 101 01389.2 filed on Jan. 13, 2001 is hereby incorporated by reference in its entirety.

EXAMPLE

The following example is intended to provide additional information towards conveying a better understanding of the invention. The Example does not limit the invention.

Synthesis of 2-methacroyloxyethylacrylate using an acidic ion exchange catalyst: 37.5 g of strongly acidic ion exchange resin (Amberlyst 35; Rohm & Haas) were dried under reduced pressure (1 mbar). 1.0 g 2,6-di-tert-butyl-4-methylphenol and 406 g methacrylic acid anhydride (technical grade: purity 91%, balance methacrylic acid and mixtures of anhydrides of acetic acid and methacrylic acids) were added. 233 g of 2-hydroxyethyl acrylate were added dropwise to the catalyst mixture over a period of 3 hours while the temperature was gradually raised from 25 to 40° C.

After complete addition of the 2-hydroxyethyl acrylate the reaction mixture was stirred for an additional 3 hours at a temperature of less than 40° C. The catalyst was separated by filtration and the resulting clear light yellow fluid was distilled under vacuum with an air purge. Subsequently methacrylic acid was removed under reduced pressure (<10 mbar) and the excess methacrylicacid anhydride was removed after further reduction in pressure. The final distillation yielded 249 gram of a clear colorless liquid with; a yield of 2-methacroyloxyethylacrylate >90%.

What is claimed is:

1. A method for preparing an asymmetric (meth)acrylate crosslinking agent comprising reacting an hydroxyacrylate of formula (II)

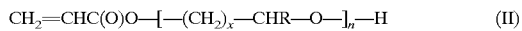

$$CH_2=CHC(O)O-[-(CH_2)_x-CHR-O-]_n-H \quad (II)$$

with methacrylic anhydride to form an asymmetric (meth)acrylate crosslinking agent of formula (I) and methacrylic acid

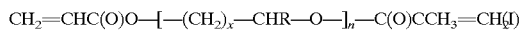

$$CH_2=CHC(O)O-[-(CH_2)_x-CHR-O-]_n-C(O)CCH_3=CH_2 \quad (I)$$

wherein, x=1, 2, or 3,

R=H or $CH_3$, and n≈1–100;

wherein a reaction product containing the asymmetric (meth)acrylate crosslinking agent comprises less than 2 wt. % of a diacrylate, dimethacrylate, or mixture thereof.

2. The method as claimed in claim 1, further comprising reacting an hydroxyacrylate of formula (II) and methacrylic acid in the presence of an acid catalyst.

3. The method as claimed in claim 2, wherein the acid catalyst is present at from 0.1 to 5 wt. %.

4. The method as claimed in claim 1, wherein the temperature is from 0 to 100° C.

5. The method as claimed in claim 1, wherein the acrylate ester and methacrylic acid are reacted for from 0.5 to 36 hours.

6. The method as claimed in claim 1, wherein x 1, R=H and the hydroxyacrylate is selected from the group consisting of diethylene glycol acrylate) triethylene glycol acrylate, tetraethylene glycol acrylate, and mixtures thereof.

7. The method as claimed in claim 1, wherein the hydroxyacrylate is a polypropylene glycol acrylate with an average molecular weight of about 475.

8. The method as claimed in claim 1, wherein the hydroxyacrylate is based on a polytetrahydrofuran chain.

9. The method as claimed in claim 8, wherein the hydroxyacrylate is 4-hydroxybutyl acrylate.

10. The method as claimed in claim 2, wherein the acid catalyst is selected from the group consisting of sulfuric acid, aromatic sulfuric acids, aliphatic sulfonic acids, aromatic sulfonic acids bound to a polymeric resin, aliphatic sulfonic acids bound to a polymeric resin, and phosphonic acids.

11. The method as claimed in claim 1, wherein a ratio of methacrylic anhydride to hydroxyacrylate is about 1:1.

12. The method as claimed in claim 1, further comprising removing methacrylic acid from a reaction mixture by distillation.

13. The method as claimed in claim 1, wherein a ratio of the hydroxyacrylate and the methacrylic anhydride is less than 1, further comprising adding a low molecular alcohol to a reaction mixture to destroy an excess of methacrylic anhydride.

14. The method as claimed in claim 1, wherein a content of impurities containing chlorine is <0.1 wt. %.

15. The method as claimed in claim 1, wherein a reaction product containing the asymmetric (meth)acrylate crosslinking agent comprises less than 1 wt. % of a diacrylate or dimethacrylate.

* * * * *